(12) United States Patent
Seligman (10) Patent No.: US 8,795,212 B2
(45) Date of Patent: Aug. 5, 2014

(54) HINGE BRACE ASSEMBLY HAVING A STRUCTURAL OUTER PLATE

(75) Inventor: Scott Seligman, San Marcos, CA (US)

(73) Assignee: DJO, LLC, Vista, CA (US)

( * ) Notice: Subject to any disclaimer, the term of this patent is extended or adjusted under 35 U.S.C. 154(b) by 627 days.

(21) Appl. No.: 12/537,418

(22) Filed: Aug. 7, 2009

(65) Prior Publication Data

US 2011/0034843 A1  Feb. 10, 2011

(51) Int. Cl.
*A61F 5/00* (2006.01)
(52) U.S. Cl.
USPC .................... 602/16; 602/20; 602/23; 602/26
(58) Field of Classification Search
USPC .......................................... 602/16, 20, 23, 26
See application file for complete search history.

(56) References Cited

U.S. PATENT DOCUMENTS

| 5,443,444 | A | 8/1995 | Pruyssers |
| 6,390,998 | B1 | 5/2002 | Doyle |
| 6,969,363 | B2 * | 11/2005 | Houser ........................... 602/16 |
| 7,192,407 | B2 * | 3/2007 | Seligman et al. ............... 602/16 |
| 2004/0153015 | A1 | 8/2004 | Seligman et al. |
| 2011/0152736 | A1 * | 6/2011 | Ng ................................. 602/16 |

FOREIGN PATENT DOCUMENTS

EP  1829507  9/2007

OTHER PUBLICATIONS

International Search Report and Written Opinion of the International Searching Authority of Application No. PCT/US2010/044744 mailed Apr. 21, 2011.

\* cited by examiner

*Primary Examiner* — Patricia Bianco
*Assistant Examiner* — Keri J Nelson
(74) *Attorney, Agent, or Firm* — Ropes & Gray LLP (57) ABSTRACT

A hinge assembly for an orthopedic brace includes, among other things, an outer plate adapted to fit over a lateral side of a hinge to protect mechanical components of the hinge. The outer plate includes an inner surface and an outer surface, and a connector housing formed below the outer surface.

21 Claims, 9 Drawing Sheets

HINGE BRACE ASSEMBLY HAVING A STRUCTURAL OUTER PLATE

BACKGROUND

Knee braces are widely used for ligament rehabilitations and for reducing potential injuries for athletes. These braces include a hinge assembly having a hinge mechanism held in place by lateral and medial hinge plates. The hinge mechanism includes various mechanical parts such as hinge arms, screws, and springs (in some cases) that allow the brace wearer to flex his calf with respect to the thigh. The lateral plate typically includes a through-hole for receiving a rivet or a screw for connecting the lateral hinge plate to the medial hinge plate. In such cases, parts of the rivets or screws are exposed to the environment, which is unsightly and less appealing to a user. To address these issues, it has become common practice for brace manufacturers to use a hinge cover to cover and protect the various mechanical components of the hinge mechanism. A hinge cover is generally made of a light weight material such as plastic or aluminum and is glued onto the lateral/medial hinge plate of the hinge assembly. The hinge cover often includes a product source identification, such as a manufacture's name and/or logo on the outer surface of the hinge cover, to help a user associate the manufacture's brand with the brace. However, over the course of regular use, the cover often comes off from the hinge assembly and exposes the inner components of the hinge mechanism. A user's confidence in the quality of the brace may be reduced when the user sees a brace without a cover.

Figure 1:
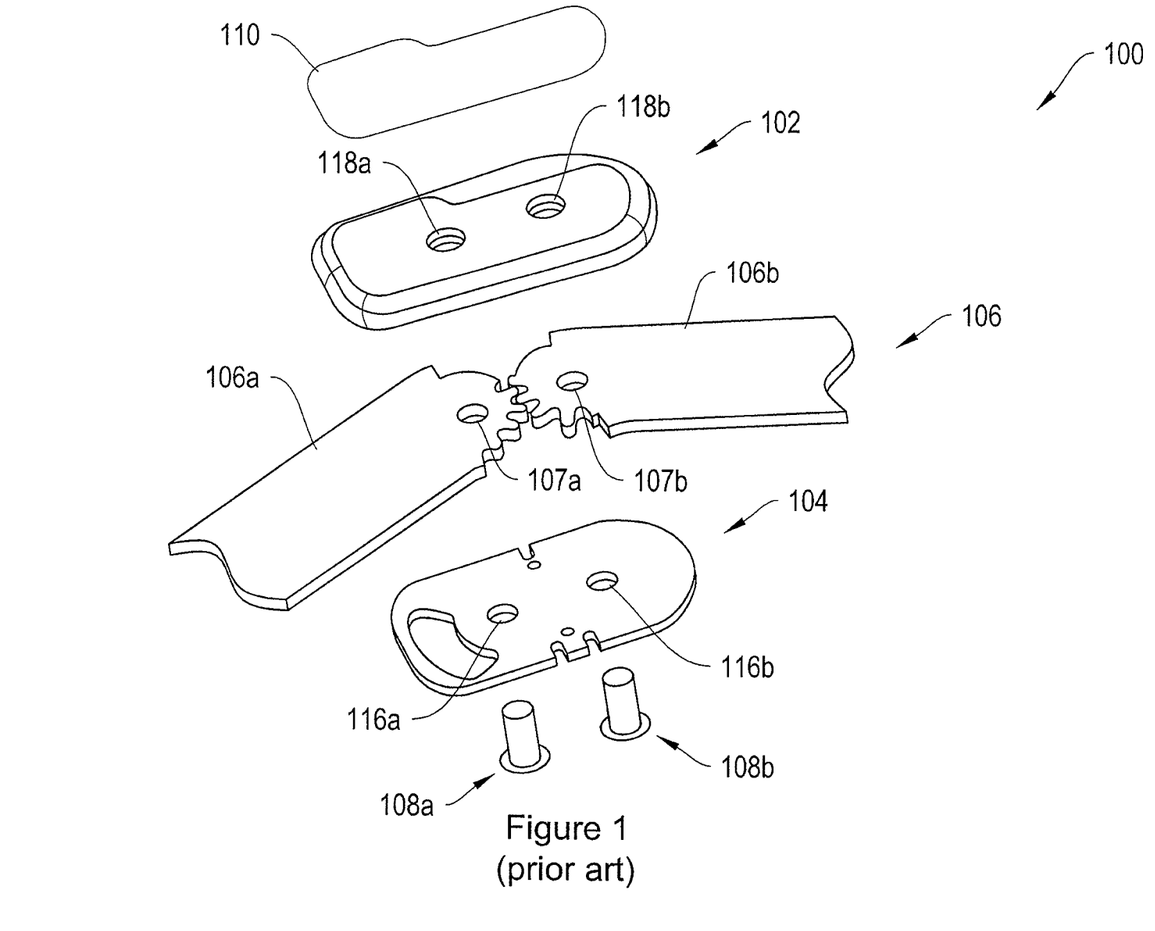
FIGS. 1-2 depict exploded views of a prior art hinge brace assembly.

FIG. 1 illustrates an exploded view of an exemplary prior art hinge brace assembly 100 that has such drawbacks. As shown, the hinge brace assembly 100 includes an outer plate 102 and an inner plate 104 for matingly engaging a hinge mechanism 106, which includes a first hinge arm 106a and a second hinge arm 106b. The hinge brace assembly 100 also includes a set of connecting members 108a and 108b (e.g., rivets or screws) for securing the hinge mechanism 106 between the inner and outer plates. The connecting member 108a is received through the holes 116a, 107a, and 118a positioned on the inner plate 104, the first hinge arm 106a, and the outer plate 102, respectively. Similarly, the connecting member 108b is received through the holes 116b, 107b, and 118b positioned on the inner plate 104, the second hinge arm 106b, and the outer plate 102, respectively. The connecting members 108a and 108b engage the hinge mechanism 106 between the inner plate 104 and the outer plate 102. The hinge brace assembly 100 also includes a thin, aluminum or plastic brace cover 110 adapted to cover and protect the inner mechanical components (e.g., outer plate 102 and the connecting members 108a and 108b).

Figure 2:
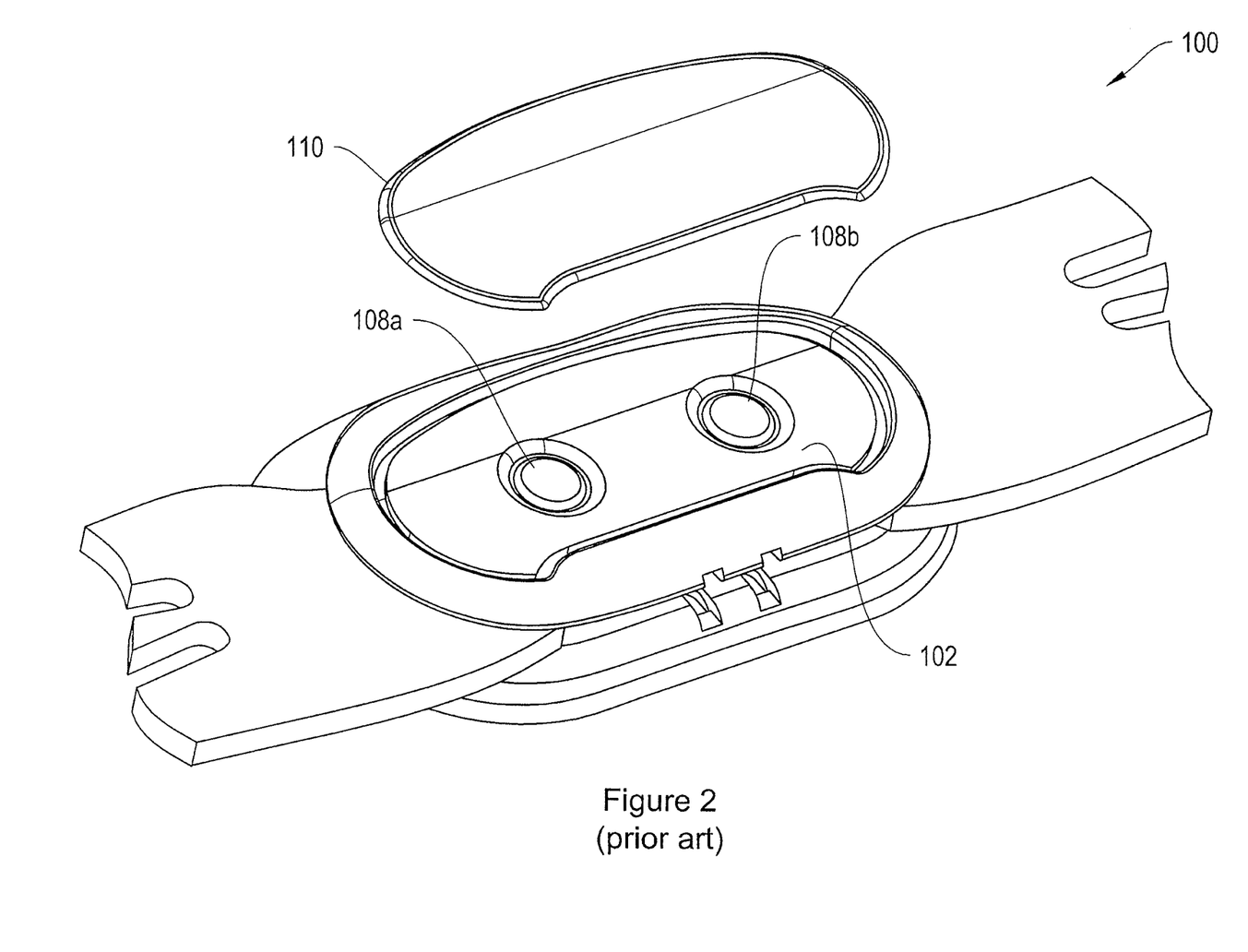

The brace cover 110 is attached to the outer plate 102 after the inner plate 104 and the outer plate 102 are fitted to one another, enclosing the hinge mechanism 106 therebetween. The brace cover 110, made of plastic or aluminum, is glued or screwed onto the outer plate 102. FIG. 2 shows an exemplary embodiment of the brace cover 110 being fitted onto the outer plate 102. The brace cover 110, in addition to protecting the mechanical components of the hinge assembly, provides an aesthetically pleasing finish to the hinge brace and may have a manufacturing logo or brand marked thereon. Under regular use, the brace cover 110 can disengage from the outer plate 102, exposing the inner mechanical components. Once disengaged, it is often difficult for a brace wearer to reattach the brace cover 110 on the outer plate 102.

The brace described herein addresses these and other limitations by providing a brace with an improved hinge cover that is less likely to be removed from the hinge assembly once assembled. Such improved hinge cover better retains the brand name and logo on a brace, which may boost a user's confidence level in the quality of the brace and render the brace more aesthetic to the user. Additionally, the improved hinge cover may better protect the inner workings of the hinge mechanism.

SUMMARY OF THE INVENTION

The hinge brace assembly disclosed herein address various deficiencies in the prior art by, in various embodiments, providing a hinge assembly that provides more reliable protection to a hinge mechanism. In one representative embodiment, a hinge assembly for an orthopedic brace is provided with an outer plate adapted to fit over a lateral side of a hinge to protect the mechanical components of the hinge. The outer plate includes an inner surface, an outer surface, and a connection port spaced beneath the outer surface. The hinge assembly includes a connecting member that engages the connection port. The hinge assembly also includes first and second hinge arms that are pivotably secured to the outer plate. In certain embodiments, the connecting member joins the first and second hinge arms to the outer plate.

In certain exemplary embodiments, the connection port includes one or more connector housings that protrude from the inner surface and forms a receptacle that receives the connecting member. In certain embodiments, the connection port has an inner surface configured to engage with a portion of the connecting member. In certain embodiments, the connection port includes a connector housing that is co-formed with the inner surface of the outer plate. In certain embodiments, the connection port includes a connector housing that is separately connected to the outer plate. In certain embodiments, the connection port is a tapped hole.

In certain exemplary embodiments, the connection port includes a channel for guiding the connecting member to the connector housing. In certain embodiments, the channel is defined by a floor surface embedded within the outer plate. In certain embodiments, the connection port includes an open end and a closed end, and a connecting member that extends through the open end.

According to certain embodiments, the hinge brace assembly also includes an inner plate adapted to matingly engage with the outer plate. The inner plate includes a recess adapted to receive the outer plate. The inner plate also includes at least one hole positioned to align with a shaft of the connecting member.

According to certain embodiments, the outer plate is configured to receive first and second shafts of the connecting member, where the first and second shafts are spaced apart. The first hinge arm is pivotably secured about the first shaft and the second hinge arm is pivotably secured about the second shaft. In certain embodiments, the connecting member includes a first shaft and a second shaft positioned on opposite sides of gear teeth formed on the first and second hinge arms.

According to certain embodiments, the hinge assembly includes an outer plate where a label is etched directly onto the outer surface of the outer plate. In certain embodiments, the outer plate is injection molded.

According to some embodiments, a hinge brace assembly for an orthopedic brace includes an outer plate adapted to fit over a lateral side of a hinge to cover mechanical components of the hinge, where the outer plate includes an inner surface and an outer surface, the outer surface covering the mechanical components of the hinge without using a separate cover. The hinge brace assembly also includes first and second hinge arms that are pivotably secured to the outer plate.

According to some embodiments, a hinge assembly for an orthopedic brace includes a label identifying the orthopedic brace's manufacturer. The label includes a perimeter surface and an inner surface and a plurality of anchoring points formed on the inner surface and interior from the perimeter surface. The hinge assembly is also provided with first and second hinge arms that are pivotably secured to the label and an inner plate for housing the first and second hinge arms. The anchoring points join the first and second hinge arms to the inner plate.

These and other features and advantages of the invention are described in further detail below with regard to illustrative embodiments.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting.

DESCRIPTION OF EXEMPLARY EMBODIMENTS

To provide an overall understanding of the invention, certain illustrative embodiments will now be described, including exemplary embodiments of an outer plate and a hinge brace assembly. However, it will be understood by one of ordinary skill in the art that the devices and methods described herein may be adapted and modified for other suitable applications and that such other additions and modifications will not depart from the scope hereof.

A hinge brace assembly described herein is a component of a brace assembly used with prophylactic knee braces (e.g., a knee brace worn about healthy knees). It may also be adapted for bracing parts of the body other than the knee. Those of skill in the art will appreciate that the hinge brace assembly described herein may be used in a variety of braces such as braces for treating osteoarthritis.

Figure 3:
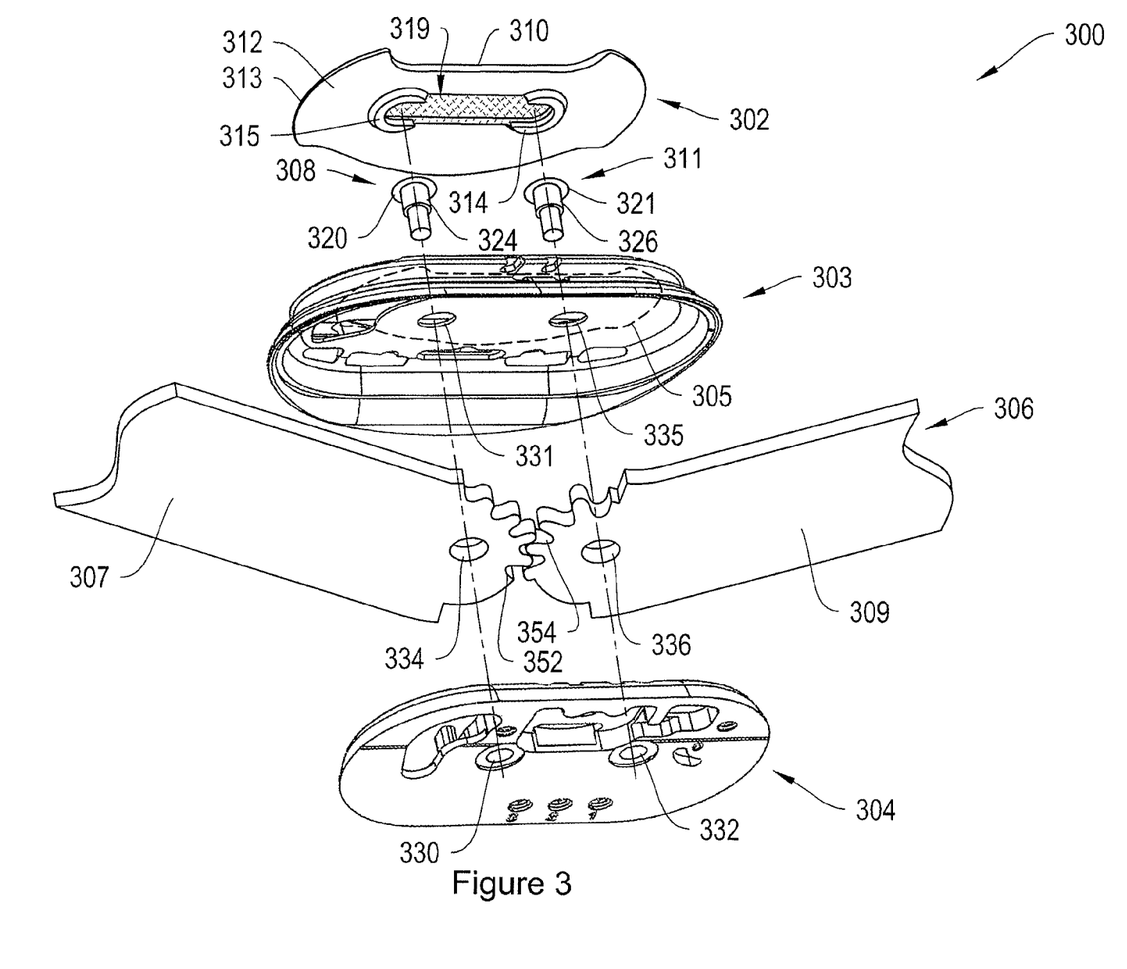
FIG. 3 depicts an exploded view of a hinge assembly according to an illustrative embodiment of the invention.

Turning to the illustrative embodiments, FIG. 3 shows an exploded view (shown from the bottom) of a hinge brace assembly 300 that addresses the problems discussed above.

As shown, the hinge brace assembly 300 includes an outer plate 302, an outer plate housing 303 for receiving and housing the outer plate 302, and an inner plate 304 for securing a hinge mechanism 306. The hinge brace assembly 300 also includes first and second hinge arms 307 and 309 pivotably secured to the outer plate 302. The outer plate 302 is adapted to fit over a lateral side of a hinge to protect the inner mechanical components of the hinge (e.g., the hinge mechanism 306 and one or more connecting members used to join the plates). The outer plate 302 also includes an inner surface 312, an outer surface 310, and a connection port 319, which includes a plurality of connector housings 314 and 315 spaced beneath the outer surface 310 (as further discussed below) for receiving one or more connecting members. As shown, the outer surface 310 of the outer plate 302 is contoured and has a perimeter surface 313 that is shaped to fit within a recess 305 disposed on the outer plate housing 303.

As shown, the hinge brace assembly 300 also includes first and second connecting members 308 and 311 for securing the outer plate 302 to the inner plate 304. These connecting members are made of stainless steel or other durable material that can withstand shearing and other forces during operation of the hinge mechanism 306. The connecting members 308 and 311 have respective shafts 324 and 326 and caps 320 and 321 that protrude from the perimeter of the respective shafts. As shown, the outer plate housing 303 includes mating holes 331 and 335 and the inner plate 304 includes mating holes 330 and 332. These mating holes are configured to receive the shafts 324 and 326, respectively, of the connecting members 308 and 311. The hinge mechanism 306 includes a first hinge arm 307 having a hole 334 and a second hinge arm 309 having a hole 336. These holes align with the mating holes of the outer plate housing 303 and the inner plate 304. More specifically mating holes 331 and 330 receive the first shaft 324 of the first connecting member 308 and the mating holes 335 and 332 receive the second shafts 326 of the second connecting member 311 to allow the first hinge arm 307 to pivot about the first shaft 324 and the second hinge arm 309 to pivot about the shaft 326 of the second connecting member 311. As shown in FIG. 3, the first connecting member 308 and the second connecting member 311 are positioned on opposite sides of gear teeth 352 and 354 that are formed on the first and second hinge arms 307 and 309, respectively.

As shown, the hinge brace assembly 300 does not include a cover over the outer surface of the plate 302. The outer plate 302 is a unitary durable plate having an outer surface 310 that covers and protects the inner mechanical components of the hinge assembly, thereby eliminating the need to use a cover that may come off with regular use. The outer plate 302, in certain embodiments, is made of stainless steel or other durable material for protecting the hinge mechanism and forming a sturdy hinge brace assembly. Compared to a plastic hinge cover, such outer plate 302 provides more structural support to the hinge brace assembly.

Figure 4A:
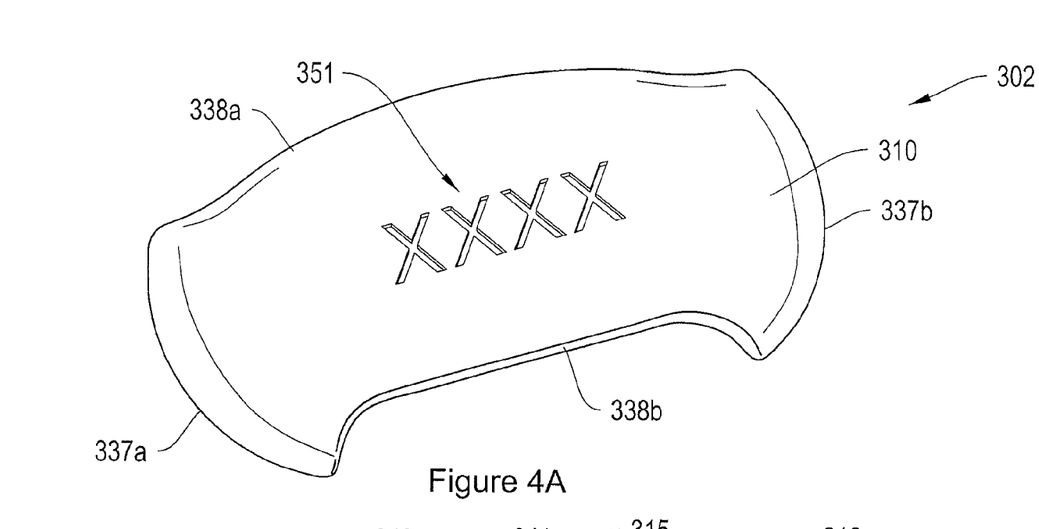
FIGS. 4A-4B depict top and bottom views of an exemplary embodiment of an outer plate according to an illustrative embodiment of the invention.
Figure 4B:
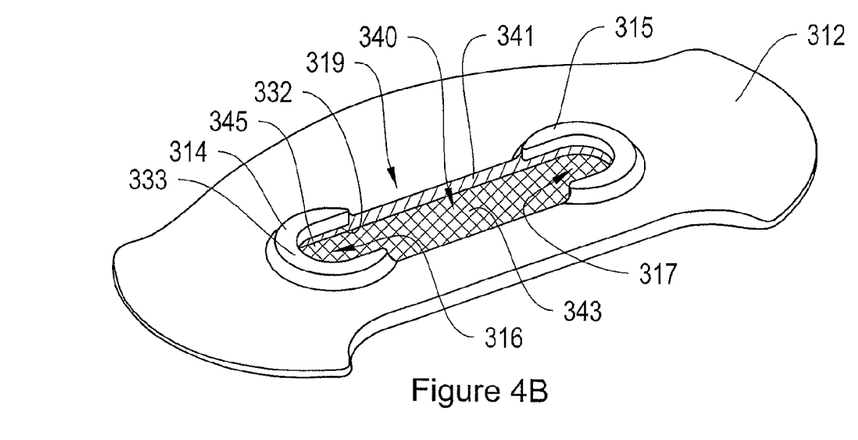

FIGS. 4A and 4B show top and bottom views of the outer plate 302. As shown in FIG. 4A, the outer surface 310 of the outer plate 302 extends continuously from a distal edge 338b to a proximal edge 338a and from a first edge 337a to a second edge 337b. As can be seen, the outer surface completely covers and protects rivets, screws or other connecting components positioned below the outer surface 310. In certain embodiments, as illustrated in FIG. 4A, the outer plate 302 includes a label 351 engraved or marked thereon to identify the brace manufacturer's brand. The label 351 may be directly formed on the outer surface 310 of the outer plate 302 during the injection molding process or etched after the outer plate 302 has been injection molded. A label is used to associate a product with a product manufacture. It is therefore useful and important to have a brace with the label that remains intact during the use and the life of the brace in the market place. A brace without a label may seem less attractive and, in certain cases, may make a user doubt the quality or source of the brace. Thus, a brace having a label that remains intact during the use of the brace not only better protects the inner components of the hinge mechanism, but improves brand associating capability.

The outer plate 302 having a label is adapted to permanently engage the inner plate 304, thereby preventing the hinge cover from disengaging during use. During assembly, the outer plate 302 receives a rivet or other connecting member below the outer surface 310 of the outer plate 302. The rivet or other connecting members fix the outer plate 302 in place with respect to the inner plate 304 (FIG. 3). More specifically, FIG. 4B shows a bottom view of the outer plate 302 having a connection port 319 spaced beneath the outer surface 310 to receive the connecting members 308 and 311. As shown, the connection port 319 includes the connector housings 314 and 315 that are formed on the inner surface 312 and protrude from the inner surface 312. In certain embodiments, the connector housings are co-formed with the inner surface (e.g., the connecting housings are formed with the outer plate when the outer plate is injection molded). In certain embodiments, the connector housings are welded or otherwise affixed to the inner surface 312 after the outer plate 302 has been formed.

The connection port 319 includes an open end defined by a channel 340 and a closed end formed by the connector housings 314 and 315. The channel 340 guides the connecting members 308 and 311 to the connector housings 314 and 315 such that the connecting members 308 and 311 extend through the open end (e.g., the channel 340). More particularly, as shown in FIG. 4B, the connector housings 314 and 315 are spaced apart by the channel 340 and these housings 314 and 315 and the ends of the channel 340 define receptacles 316 and 317 that receive the connecting members 308 and 311 (FIG. 3), as discussed below.

As shown, the receptacle 316 includes an interior rim 332 and an exterior platform 333. The receptacle 316 is also defined by a receptacle surface 345 of the channel 340. The receptacle surface 345, as shown in FIG. 4B, is part of an interior channel floor 343 of the channel 340. As shown, the channel 340 is defined by the interior channel floor 343 and a perimeter side wall 341, which surrounds the interior channel floor 343 of the channel 340. In operation, the channel 340 guides the connecting member 308 to the receptacle 316 and secures the connecting member 308 within the receptacle 316. The receptacle 316, in the illustrated embodiment, is a slot adapted to receive the connecting members. The receptacle 317 is similarly configured.

Figure 5:
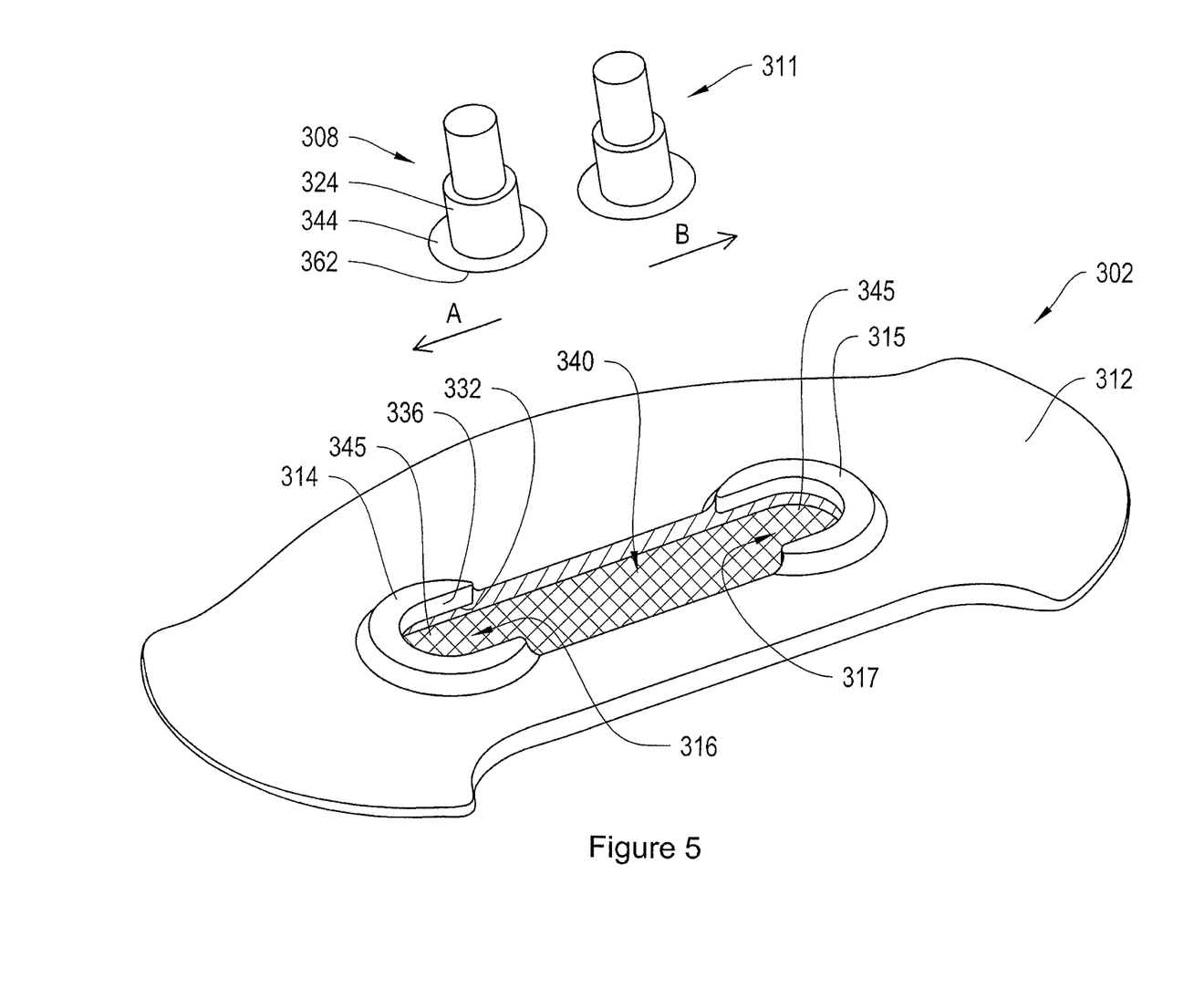
FIG. 5 shows an exemplary mating relationship between an outer plate and a plurality of connecting members as shown in FIG. 3.

FIG. 5 shows a bottom view of the outer plate 302 and connecting members 308 and 311 configured to be engaged within the receptacles 316 and 317 of the outer plate 302. During an exemplary product assembly process, the connecting members 308 and 311 are inserted into the channel 340 and slide into the respective connector housings 314 and 315 in the direction noted by Arrows A and B, respectively. When the connecting member 308 is fully engaged within the connector housing 314, an inner wall 336 of the connector housing 314 abuts a portion of the shaft 324, and the cap 344 of the connecting member 308 aligns with the inner rim 332 of the connector housing 314. The connecting member 308 also includes a top head surface 362, which abuts the receptacle surface 345 of the interior channel floor 343.

Figure 6:
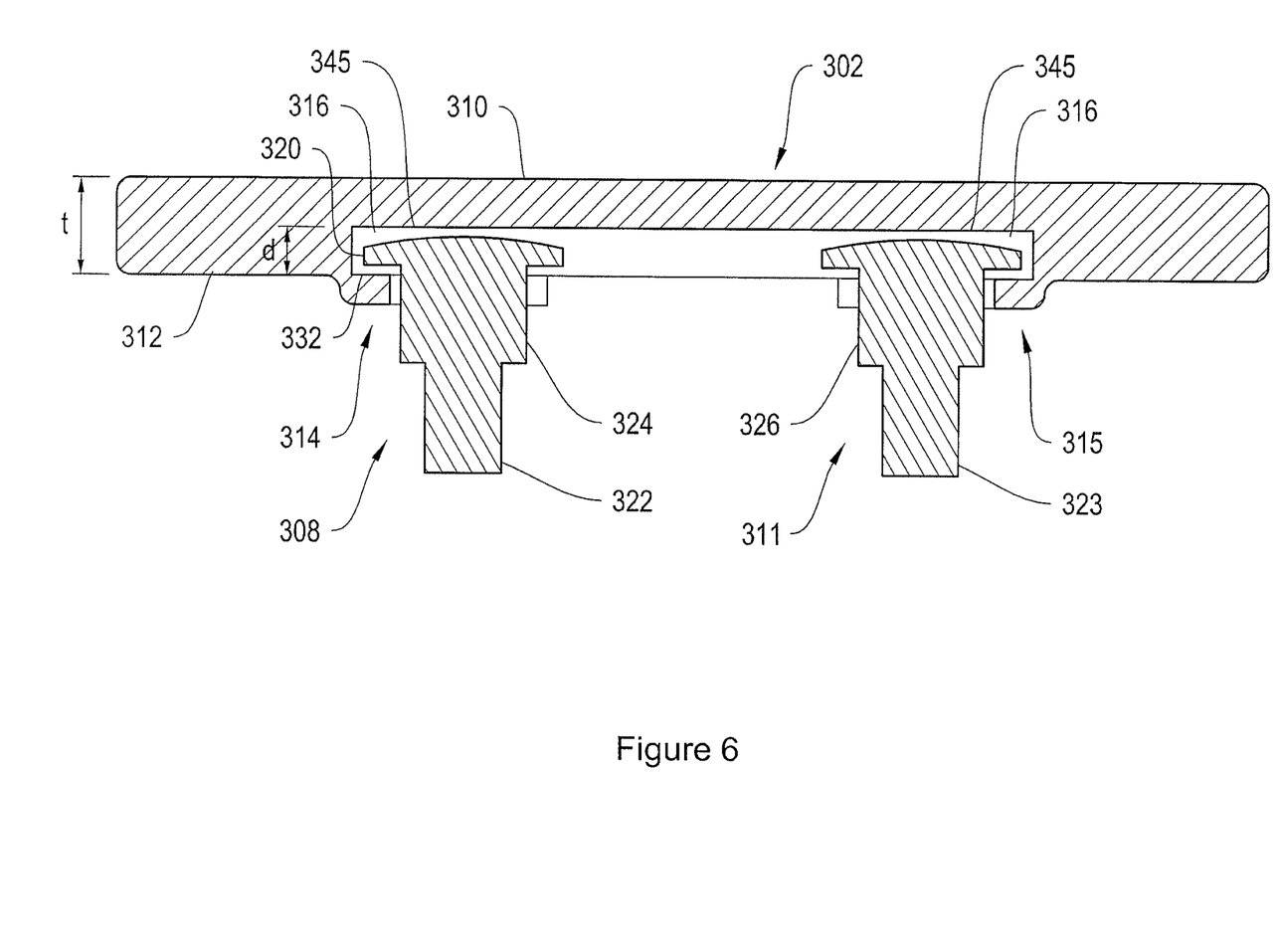
FIG. 6 depicts a cross sectional view of the connecting members being engaged to the outer plate as shown in FIG. 5.

FIG. 6 shows a cross sectional view of the connecting members 308 and 311 engaged with the outer plate 302. As shown in FIG. 6, the receptacle 316 is adapted to receive a head portion 320 of the connecting member 308. The connecting member 308 is held in place by the receptacle surface 345 and the inner receptacle rim 332 of the connector housing 314. The connection between connecting member 311 and receptacle 317 of the connector housing 315 is similar to that described above.

As shown, the receptacle 316 extends a distance d into the outer plate 302, as measured from the inner surface 312 of the outer plate 302 to the receptacle surface 345. The distance d is less than the thickness t of the outer plate 302. The interior channel floor 343 of the channel 340 is therefore located below the outer surface 310 of the outer plate 302. Thus, the housing 314 that holds the connecting member 308 is spaced beneath the outer surface 310, thereby protecting the connecting member from the environment by the outer plate 302. More specifically, the outer surface 310 of the outer plate 302 protects and covers the underlying mechanical components of the hinge, which may strengthen and prolong the life of the hinge brace assembly.

Figure 7:
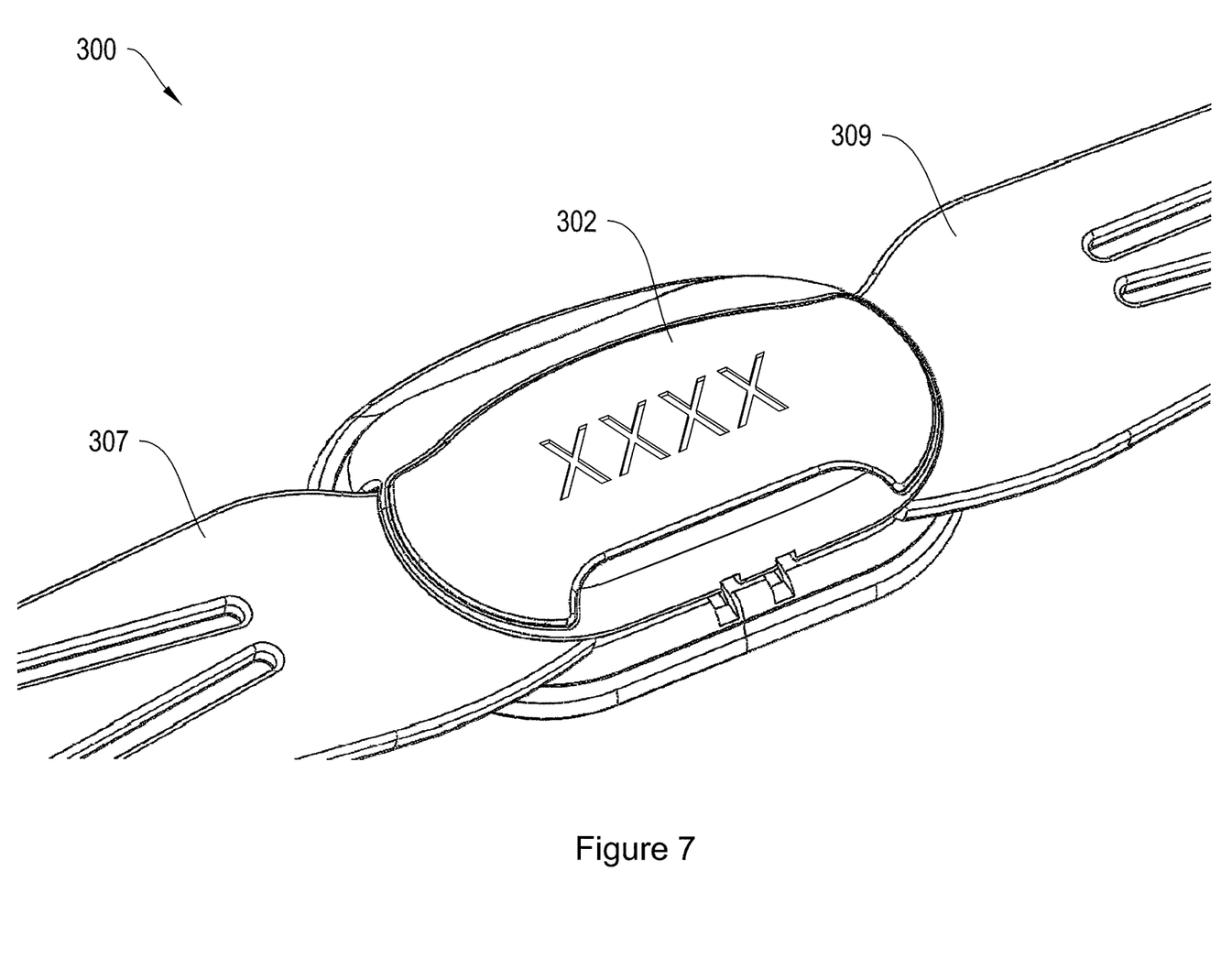
FIG. 7 depicts a perspective view of the hinge assembly shown in FIG. 3.

The outer plate embodiment shown in FIG. 6 is fitted within the outer plate housing 303 (FIG. 3) and joins with the hinge mechanism 306 (FIG. 3) and the inner plate 304 (FIG. 3) to form the hinge brace assembly 300. This is done, as discussed above, as the outer plate hosing 303, the hinge mechanism 306, and the inner plate 304 engage the shafts 324 and 326, respectively, of the connecting members 308 and 311. After such engagement, the tail end portions 322 and 323 of the connecting members 308 and 311 are crimped to permanently fix the outer plate 302 to the inner plate 304. FIG. 7 shows an exemplary embodiment of the hinge brace assembly 300.

Figure 8:
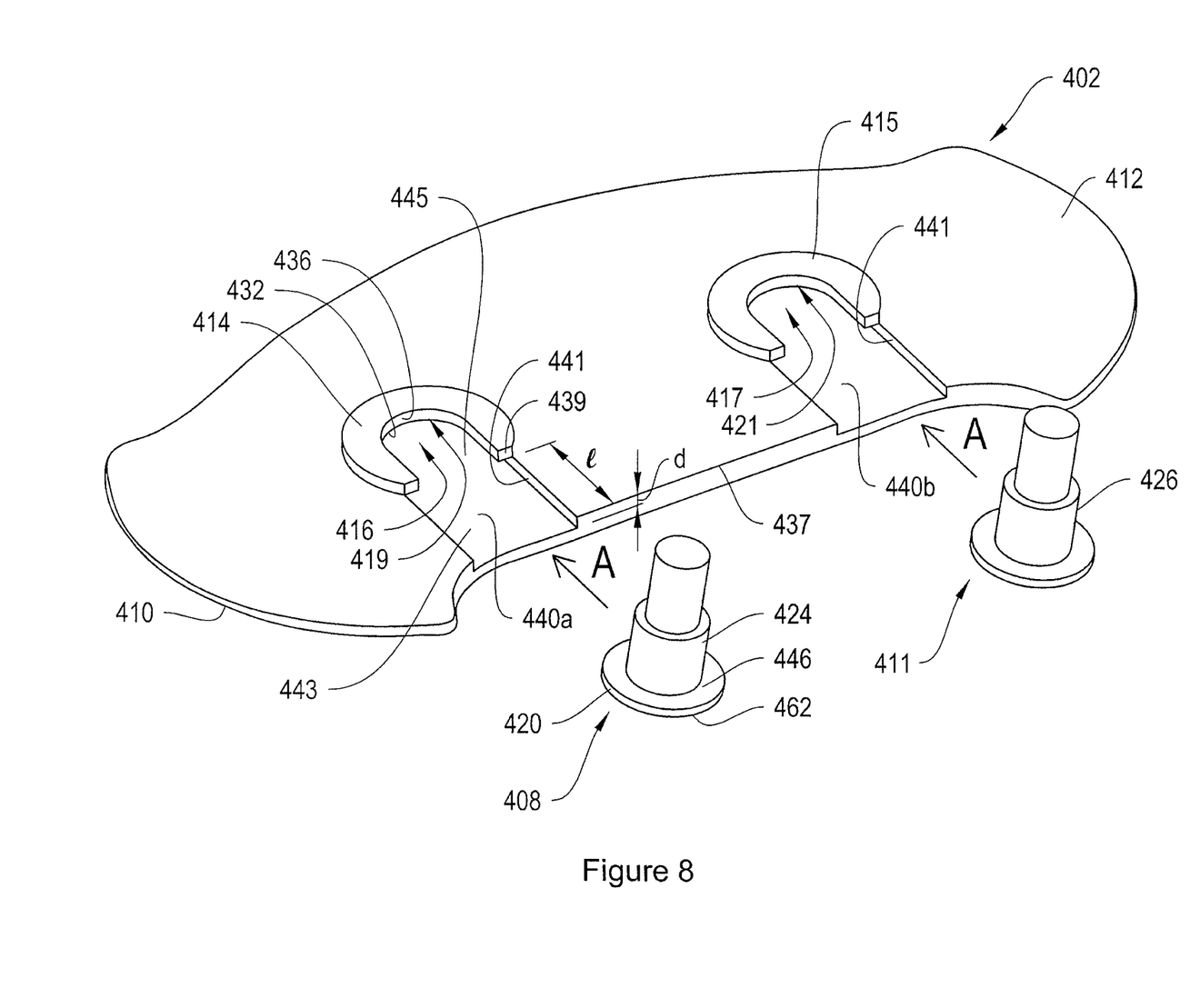
FIG. 8 shows an alternative embodiment of an outer plate and the connecting members according to an illustrative embodiment of the invention.

FIG. 8 shows an alternative embodiment of an outer plate and a plurality of connecting members 408 and 411. As shown, the outer plate 402 includes an inner surface 412 and an outer surface 410. Similar to the outer plate 302 shown in FIG. 5, the outer surface 410 extends continuously and does not have mechanical components protruding through the outer surface 410. The outer plate 402 also includes a set of connector housings 414 and 415 positioned beneath the outer surface 410 and formed with the inner surface 412, similar to the connections discussed above. The connector housings 414 and 415 protrude from the inner surface 412 and define receptacles 416 and 417 adapted for receiving the connecting members 408 and 411. The receptacles 416 and 417 are each surrounded by the perimeter walls 419 and 421, respectively. The receptacles also join separate channels 440a and 440b that are each defined by a perimeter wall 441. The channels 440a and 440b guide the connecting members 408 and 411 to the receptacles 416 and 417, respectively, formed by the connector housings 414 and 415. As shown, each channel has a channel floor 443 that includes a receptacle surface 445 located within the respective receptacle.

The channel 440a is adapted to receive a head portion 420 of the connecting member 408 that slides into the receptacle 416 in the direction noted by Arrow A. When the connecting member 408 is fully engaged with the connector housing 414, an inner surface 436 of the connector housing 414 abuts a portion of the shaft 424 and an inner head surface 446 of the connecting member 408 aligns with inner rim 432 of the connector housing 414. The connector housing 408 also includes a top head surface 462, which engages the receptacle surface 445 when fully mated. Once the connecting members 408 and 411 are fully engaged with the outer plate 402, a hinge mechanism (e.g., hinge mechanism 306 as shown in FIG. 3) and an inner plate (e.g., inner plate 304 as shown in FIG. 3) are joined to the outer plate 402 in a similar manner as shown in FIG. 3.

As shown, the connector housing 414 is mounted above the channel 440a beginning at a location that extends a distance l from the distal edge 437 of the outer plate 402 to a distal edge 439 of the connector housing 414. The channels 440a and 440b extend to a depth d below the inner surface 412, as noted in FIG. 8. As shown, the connecting members do not protrude through the outer surface 410 of the outer plate 402 as the channels 440a and 440b only extend to a distance d, which is a fraction of the thickness of the outer plate 302.

Figure 9:
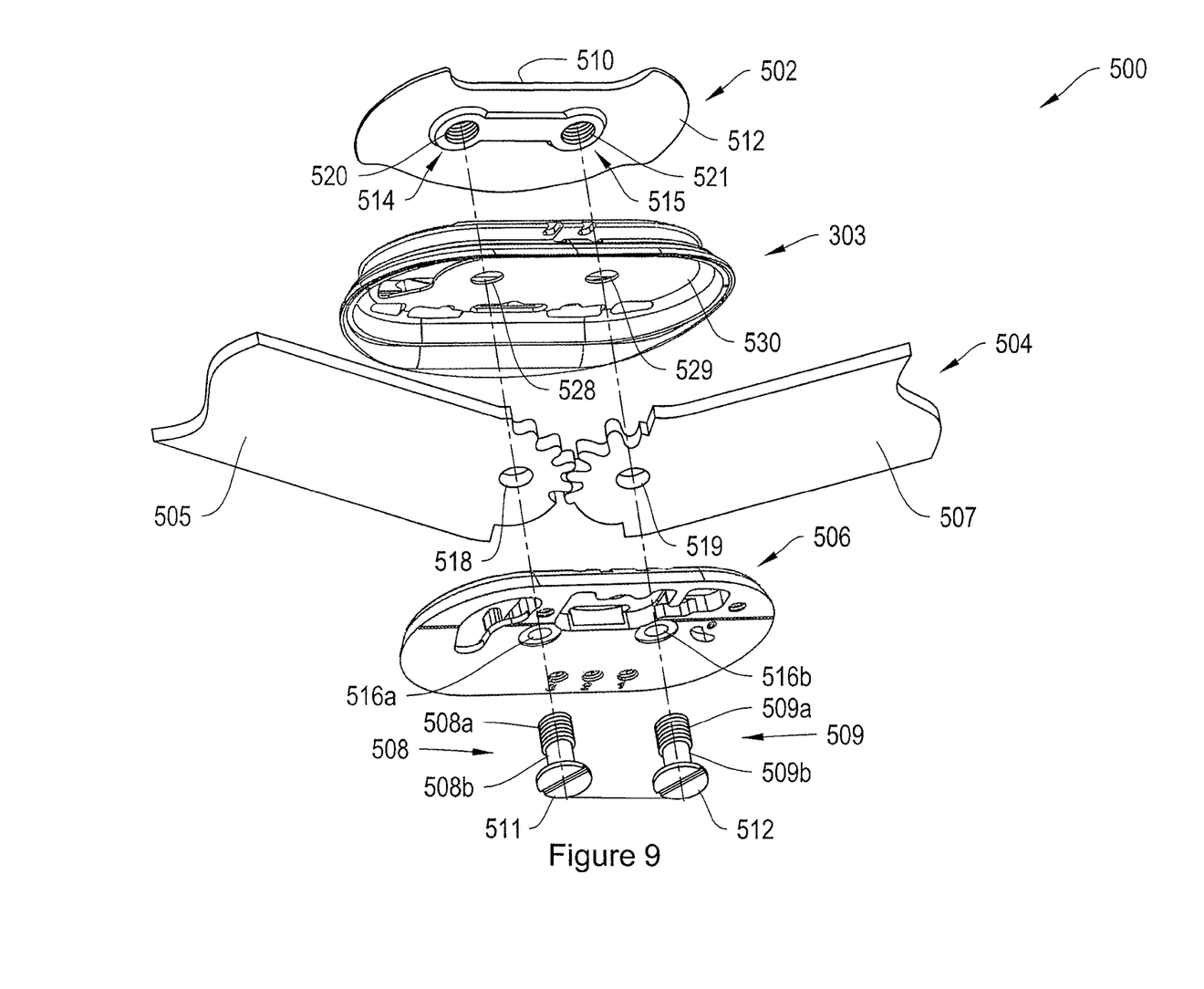
FIG. 9 shows an exploded view of an alternative embodiment of a hinge brace assembly according to an illustrative embodiment of the invention.

FIG. 9 shows an alternative embodiment of a hinge brace assembly. As shown, a hinge brace assembly 500 includes an outer plate 502, an outer plate housing 503 for securing the outer plate 502, a hinge mechanism 504, and an inner plate 506. The outer plate 502 is a unitary component having an outer surface 510 that extends continuously without protruding mechanical components, and without gaps or holes, from one end to the other end. The outer plate 502 also includes an inner surface 512 and a plurality of threaded connector housings 514 and 515 that are spaced beneath the outer surface 510. These connector housings are adapted to receive the connecting members 508 and 509 and engage the outer plate 502 with the inner plate 506, while matingly enclosing the hinge mechanism 504. This is done as threaded portions 520 and 521 of the connector housings 514 and 515 receive connecting members 508 and 509, which have complimentary threads. In particular, the connecting members 508 and 509 include threaded portions 508a and 509a and solid shaft portions 508b and 509b. The threaded portion 508a and 509a engage the threaded portions 520 and 521 of the connector housings 514 and 515, which connects the inner plate 506 to the outer plate 502 while pivotally securing first and second hinge arms to the outer plate 502.

Such connection is made by the holes 516a and 516b in the inner plate 506 and the holes 518 and 519 in the hinge arms 505 and 507 and holes 528 and 529 disposed on the outer plate housing 503. As shown, these holes are sized and shaped to receive the solid shaft portions 508b and 509b of the connecting members 508 and 509, respectively. Holes 516a, 518, and 528 align with the solid shaft portion 508b of the connecting member 508. Similarly, holes 516b, 519, and 529 align with the solid shaft portion 509b of the connecting member 509. As shown, the outer plate housing 503 also includes a pocket 530 shaped to receive the first and second hinge arms 505 and 507. Once all of these components are assembled, the first hinge arm 505 pivots about the connecting member 508 and the second hinge arm 507 pivots about the connecting member 509.

A separate cover may be used in addition to the outer plate. For example, a separate cover may be applied over the outer plate to include or hide a particular brand logo. However, similar to the hinge brace assembly 300 shown in FIG. 3A, the hinge brace assembly 500 does not need a separate cover to protect the inner mechanical components of the hinge mechanism 504 as the connector housings 514 and 515 are positioned below the outer surface 510 of the outer plate 502. The outer surface 510, which extends continuously and without gaps or holes, acts as a "built-in" cover to protect the inner mechanical components of the hinge mechanism 504 and the outer plate 502.

In certain embodiments, the hinge brace assembly includes an intermediate connector, which is separately attachable to the outer plate and detachable therefrom, for joining a connecting member (e.g., rivet or a screw) to the outer plate. In other words, the connecting member (e.g., rivet or screw) joins the outer plate through the intermediate connector and not directly to the outer plate. In certain embodiments, the intermediate connector is a hollow cylindrical shaft having a thread formed on the outer surface. Such intermediate connector joins to the outer plate, which includes complementary threads to receive the intermediate connector. In certain embodiments, the outer plate includes a tapped hole that extends from the inner surface of the outer plate towards the outer surface of the outer plate. The tapped hole, however, does not protrude through the outer plate. After the intermediate connector is joined to the outer plate (e.g., the outer thread formed on the intermediate connector mating with the threads formed on the tapped hole positioned on the outer plate), such assembly is now ready to receive a connecting member (e.g., rivet or screw). In such embodiment, the intermediate connector includes an inner thread or a receptacle (e.g., receptacle 316 shown in FIG. 6) for joining the connecting member to the intermediate connector. In use, after a connecting member is joined to the intermediate connector, a hinge mechanism (e.g., hinge mechanism 306) and an inner plate (e.g., inner plate 304) joins the shafts of the connecting members to form a hinge brace assembly.

In alternative embodiments, a single connecting member joins the inner plate to the outer plate while enclosing a hinge mechanism between the plates. In certain implementations, first and second hinge arms of the hinge mechanism pivot about the shaft of the single connecting member. In certain embodiments, the connecting member (e.g., a single screw or a pin) protrudes through the inner plate, both of the hinge arms, and partially into the outer plate. The connecting member does not protrude through the outer plate. The connecting member is then permanently fixed to the outer plate, thereby fixing the inner plate to the outer plate and enclosing the hinge mechanism therebetween.

It is to be understood that while the invention has been described in conjunction with the various illustrative embodiments, the forgoing description is intended to illustrate and not limit the scope of the invention. For example, a variety of systems and/or methods may be implemented based on the disclosure and still fall within the scope of the invention. Other aspects, advantages, and modifications are within the scope of the following claims. All references cited herein are incorporated by reference in their entirety and made part of this application.

What is claimed is:

1. A hinge assembly for an orthopedic brace, comprising:
   an outer plate that fits over a lateral side of a hinge to protect mechanical components of the hinge;
   the outer plate comprising an inner surface, an outer surface, and a connection port formed on the inner surface and extending therefrom;
   a connecting member that engages the connection port, wherein the connection port includes a connector housing and a channel that guides the connecting member to an opening of the connector housing; and
   first and second hinge arms pivotably secured to the outer plate by the connecting member.

2. The hinge assembly of claim 1, wherein the connection port has an inner surface configured to engage with a portion of the connecting member.

3. The hinge assembly of claim 1, wherein the connecting member joins the first and second hinge arms to the outer plate.

4. The hinge assembly of claim 1, wherein the channel is defined by a floor surface embedded within the outer plate.

5. The hinge assembly of claim 1, wherein the outer surface of the outer plate has a contoured perimeter.

6. The hinge assembly of claim 1, wherein the connecting member is a rivet or a screw.

7. The hinge assembly of claim 1, comprising an inner plate that matingly engages with the outer plate.

8. The hinge assembly claim 7, wherein the inner plate includes at least one hole positioned to align with a shaft of the connecting member.

9. The hinge assembly of claim 1, further comprising an outer plate housing having a recess that receives the outer plate.

10. The hinge assembly of claim 1, wherein the outer plate is configured to receive first and second shafts of the connecting member, the first and second shafts being spaced apart.

11. The hinge assembly of claim 10, wherein the first hinge arm is pivotably secured about the first shaft and the second hinge arm is pivotably secured about the second shaft.

12. The hinge assembly of claim 1, wherein the connecting member includes a first shaft and a second shaft positioned on opposite sides of gear teeth formed on the first and second hinge arms.

13. The hinge assembly of claim 1, wherein a label is etched directly onto the outer surface of the outer plate.

14. The hinge assembly of claim 1, wherein the outer plate is injection molded.

15. The hinge assembly of claim 1, wherein the connection port includes a connector housing that is co-formed with the inner surface of the outer plate.

16. The hinge assembly of claim 1, wherein the connection port includes a connector housing that is separate from the outer plate.

17. The hinge assembly of claim 1, wherein the connection port is a tapped hole.

18. The hinge assembly of claim 1, wherein the connection port comprises an open end and a closed end, and the connecting member extends through the open end.

19. The hinge assembly of claim 1, wherein the channel guides the connecting member to the opening within the connector housing in a direction that is parallel to the inner surface.

20. A hinge assembly for an orthopedic brace, comprising:
an outer plate that fits over a lateral side of a hinge to cover mechanical components of the hinge, wherein the mechanical components comprise at least one connecting member;
the outer plate comprising an inner surface and an outer surface, the outer surface covering the mechanical components of the hinge without using a separate cover, wherein the at least one connecting member is received by a connector housing formed on and extending from the inner surface of the outer plate; and
first and second hinge arms pivotably secured to the outer plate by the at least one connecting member.

21. A hinge assembly for an orthopedic brace, comprising:
a hinge plate identifying the orthopedic brace's manufacturer comprising:
a perimeter surface and an inner surface; and
a plurality of anchoring points formed on the inner surface and interior from the perimeter surface;
first and second hinge arms pivotably secured to the hinge plate; and
an inner plate housing the first and second hinge arms;
wherein each of the anchoring points comprises an opening and a rim configured to engage connecting members that join the first and second hinge arms to the inner plate.

* * * * *